United States Patent [19]

Yoshimoto et al.

[11] Patent Number: 4,897,470
[45] Date of Patent: Jan. 30, 1990

[54] ANTHRACYCLINE ANTIBIOTICS DCP-1 AND 2

[75] Inventors: Akihiro Yoshimoto, Fujisawa; Osamu Jodo, Yokohama; Yoshio Watanabe, Fujisawa; Tomoyuki Ishikura, Chigasaki; Tsutomu Sawa, Ayase; Tomio Takeuchi, Tokyo; Hamao Umezawa, deceased, late of Tokyo, all of Japan, by Mikeo Umezawa, Kazuo Umezawa and Yoji Umezawa, heirs

[73] Assignee: Sanraku Incorporated, Tokyo, Japan

[21] Appl. No.: 34,879

[22] Filed: Apr. 6, 1987

[30] Foreign Application Priority Data

Apr. 8, 1986 [JP] Japan .................................. 61-79264

[51] Int. Cl.$^4$ ............................................. C07H 15/24
[52] U.S. Cl. ................................................... 536/6.4
[58] Field of Search ............................. 536/6.4; 514/34

[56] References Cited

U.S. PATENT DOCUMENTS 4,734,493  3/1988  Yoshimoto et al. ................. 536/6.4

Primary Examiner—Johnnie R. Brown
Assistant Examiner—Elli Peselev
Attorney, Agent, or Firm—Jordan and Hamburg

[57] ABSTRACT

New anthracycline antibiotics of a formula (I) are provided, which are usable as an anticancer agent

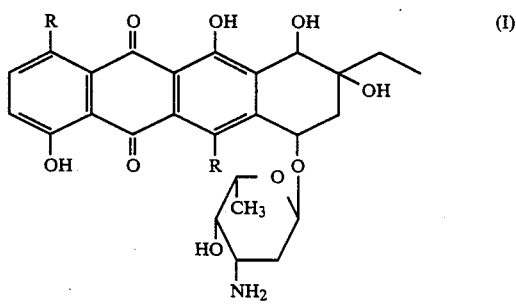

(where R represents a hydrogen atom or a hydroxyl group). The antibiotics (I) can be produced by incubation of a dye-nonproductive or hardly dye-productive mutant strain which has an ability of converting α-citromycinone or β-isorhodomycinone into the antibiotics (I), in the presence of α-citromycinone or β-isorhodomycinone in a pertinent nutrient medium.

3 Claims, No Drawings

ANTHRACYCLINE ANTIBIOTICS DCP-1 AND 2

FIELD OF THE INVENTION

The present invention relates to new anthracycline antibiotics having anticancer activity.

BACKGROUND OF THE INVENTION

As anthracycline family of antibiotics, daunomycin (refer to U.S. Pat. No. 3,616,242) and adriamycin (refer to U.S. Pat. No. 3,590,028) have heretofore been known, which can be obtained from a culture broth of actinomycetes, and these compounds have a broad tumoricidal spectra against experimental tumors and are being utilized broadly as chemotherapeutic agents for cancers treatment. However, daunomycin and adriamycin in fact show a fairly strong anticancer effect, while these have some strong side-effects such as a severe cardiotoxic effect, and therefore, these are not sufficiently satisfactory as a therapeutic agent. Accordingly, attempts to obtain the analogous compound with improved therapeutic efficacy have been made by fermentation method, semi-synthetic method, microbial transformation method and the like other various means. For instance, U.S. Pat. No. 3,988,315 illustrates aclacinomycins A and B; Journal of Antibiotics (Vol. 33, pages 1331-1340), Topics in Antibiotics Chemistry (Vol. 12, pages 102-279, published by Ellis Horwood Limited) and U.S. Pat. No. 4,355,026 illustrate 4-demethoxy-11-deoxydaunomycin; and U.S. Pat. No. 4,316,011 illustrates rhodomycin group antibiotics. ("published unexamined Japanese patent application".)

Various kinds of anthracycline antibiotics have been proposed as anticancer agents, as mentioned above; some of them have already been used for cancer chemotherapy and some others are in clinical trial. However, none of them is satisfactory both in toxicity and anticancer efficacy. Moreover, results of anticancer agents obtained with in vitro and in vivo tests using experimental tumors are not always reflective directly on anticancer effect against human and therefore, investigations are required from various viewpoints. For this reason, it has been desired to propose compounds belonging to a further new class, with respect to anthracycline antibiotics which have been evaluated in a way.

SUMMARY OF THE INVENTION

An object of the invention is to provide novel anthracycline antibiotics represented by formula (I):

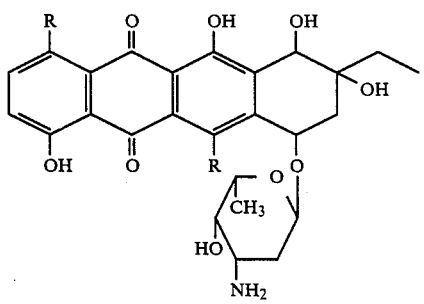

(where R represents a hydrogen atom or a hydroxyl group).

The said compounds of the formula (I) can be produced by microbial transformation of natural anthracyclinone aglycones α-citromycinone and β-isorthodomycinone) represented by formula (II):

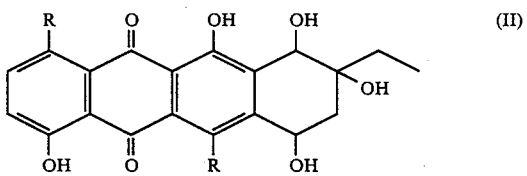

(where R represents a hydrogen atom or a hydroxyl group) with a sub-culture of an anthracycline pigment-nonproductive mutant strain which was derived from Streptomyces sp. D788, strain RPM-5 (FERM P-7703, refer to Japanese Patent Kokai No. 33194/86) proposed as a producer of new anthracycline antibiotics D788-6 to 10, and possess a highly therapeutic antitumor effect on L1120 leukemia in mice, as well as a potent inhibitory activity against proliferation of cultured L1210 cells.

DETAILED DESCRIPTION OF THE INVENTION

All of the said compounds are new anthracycline compounds which comprise rhodomycin-series aglycone and a daunosamine and which are not described in any prior art disclosures, and these were first obtained by the present inventors by means of a microbial-transformation utilizing a specific strain isolated by the present inventors. Among these compounds of the formula (I), the antibiotic of the following formula (I-a):

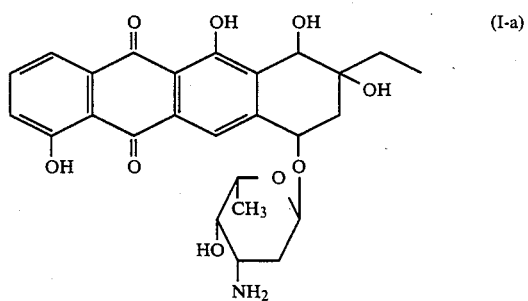

is called DCP-1; and the antibiotic of the following formula (I-b):

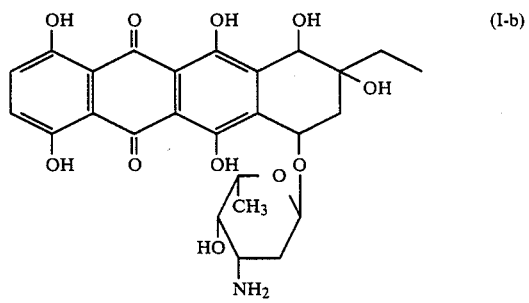

is called DCP-2, hereinafter.

These compounds exhibit a highly inhibitory effect against proliferation of cultured leukemic L1210 cells and are per se effective against L1210 leukemia in mice.

Inhibitory Action against proliferation and nucleic acid biosynthesis of cultured L1210 cells.

L1210 cells of $5 \times 10^4$/ml were inoculated into, e.g., RPM 11640 medium (Resewellberg Research Laboratories) containing 10% bovine serum and the substances of the present invention was added thereto in a concentration of 0.0005 to 0.25 µg/ml. In the addition of the said substances to the cell culture medium, these were dissolved in 1/50M acetic acid (pH 3.0) in a concentration of 1 µg/ml and then diluted with Dulbecco PBS(−) (Nissui Pharmaceutical Co.) and then added. Cultivation was performed at 37° C. for 48 hours in Napco automatic $CO_2$ incubator with humidified atmosphere containing 3.5% $CO_2$. The cell growth was measured by coulter counter and a 50%-growth inhibitory concentration was determined from a dose-inhibition curve.

On the other hand, the aforesaid L1210 cells of $5 \times 10^5$ was suspended in RPM 11640 medium supplemented with 10% bovine serum and incubated at 37° C. for 1 hour in the aforesaid $CO_2$ incubator. The said substance was added in various concentration as described above and after 15 minutes, $^{14}$C-uridine (0.05 µCi/ml) or $^{14}$C-thymidine (0.05 µCi/ml) was further added thereto and incubation was continued for further 60 minutes. A cold 10% trichloroacetic acid (TCA) was added to the cell culture to stop the $^{14}$C-incorporation and to precipitate $^{14}$C-incorporated nucleic acid as acid insoluble materials. The precipitate was collected, washed twice with cold 5% TCA by centrifugation and was dissolved in formic acid. The radioactivity of the solution was measured in Bray's scintillator. A concentration giving a 50%-incorporation inhibition was determined based on a dose-inhibition curve. The results are given in Table 1.

TABLE 1

Inhibition of growth and nucleic acid biosynthesis of leukemic L1210 cell culture by the compounds of the present invention

| Compound | 50% inhibitory concentration (µg/ml) | | |
|---|---|---|---|
| | Cell growth | DNA synthesis | RNA synthesis |
| DCP-1 | 0.006 | 0.70 | 1.00 |
| DCP-2 | 0.004 | 1.00 | 0.78 |
| Adriamycin | 0.020 | 1.40 | 0.55 |

The in vivo antitumor effects of DCP-1 and DCP-2 were examined against mice bearing L1210 leukemia and the results are shown in Table 2.

TABLE 2

Antitumor Effect of DCP-1 and DCP-2 against L1210 Leukemia

| Drug | Dose (µg/mouse/day) | T/C (%) | Therapeutic index |
|---|---|---|---|
| DCP-1 | 12.5 | 100 | 13.0 |
| | 6.25 | 120 | |
| | 3.13 | 157 | |
| | 1.56 | 188 | |
| | 0.78 | 181 | |
| | 0.39 | 181 | |
| | 0.20 | 157 | |
| | 0.10 | 126 | |
| DCP-2 | 50 | 115 | 7.4 |
| | 25 | 128 | |
| | 12.5 | 177 | |
| | 6.25 | 195 | |
| | 3.13 | 186 | |
| | 1.56 | 159 | |
| | 0.78 | 128 | |
| | 0.39 | 110 | |
| ADM* | 100 | 130 | 3.1 |
| | 50 | 200 | |
| | 25 | 275 | |
| | 12.5 | 168 | |
| | 6.25 | 145 | |
| | 3.13 | 124 | |

Animal: $CDF_1$ mice
Tumor inoculation: $1 \times 10^5$ cells/mouse
Treatment: day 1 to 10
Therapeutic index: ratio of doses given T/C max and T/C 130%
*Adriamycin (reference)

The said compounds can be produced by cultivating a pigment-nonproductive mutant strain, which can be derived from newly isolated microorganisms or known microorganisms belonging to actinomycetes capable of producing daunomycin or carminomycin or related anthracycline antibiotics by a conventional mutagenic treatment with mutagen, for example, such as ultraviolet light or N-methyl-N'-nitro-N-nitrosoguanidine (NTG), in the present of α-citromycinone or β-isorhodomycinone.

One typical example of such a mutant strain capable of converting α-citromycinone or β-isorhodomycinone to DCP-1 or DCP-2 is strain OXA-4 as obtainable from the above-mentioned Streptomyces sp. D788, strain RPM-5, which was described in prior Japanese Patent Application as a producer of new daunomycin analogues, by NTG mutation.

The said strain was deposited under FERM P-8708 on Mar. 22, 1986 at Fermentation Research Institute (Japan), Agency of Industrial Sciences and Technology, 1-3, Higashi, 1-chome, Yatabe-machi, Tsukuba-gun, Ibaraki-ken, Japan and transferred on Apr. 3, 1987 to international deposition FERM BP-1330 under the Treaty on the International Recognition of the Deposit of Microorganisms for the Purpose of Patent Procedure.

Hereinafter, the micrological properties of the strain OXA-4 are described below.

(i) Morphological characteristic:

Linear aerial hyphae are developed from branched substrate hyphae but no whirl is formed. Matured spores in a chain of 10 or more have a diameter of about 0.6 to $0.8 \times 0.9$ to $2.5\mu$. The spore surface is smooth. Neither ascospore nor flagella spore is formed.

(ii) Growth conditions in various media:

With respect to color indication, the standard shown within parenthesis is based on "System of Color Wheels for Streptomyces Taxonomy" written by Tresner & E. J. Backus (J. Appl. Microbiol, Vol. 11, pages 335–338, 1963), which is supplemented by "Color Standard" published by Nippon Color Research Laboratories.

TABLE 3

Growing state in various media (28° C.)

| Medium | Growth | Aerial hyphae | Substrate hyphae | Soluble pigment |
|---|---|---|---|---|
| Sucrose Nitrate Agar medium | Middle | Slightly violetish white (13ba) | Slightly violetish white (13ba) | None |
| Glucose Asparagine Agar medium | Good | Not formed | White (a) | None |
| Glycerin | | Slightly | | |

TABLE 3-continued

| | Growing state in various media (28° C.) | | | |
|---|---|---|---|---|
| Medium | Growth | Aerial hyphae | Substrate hyphae | Soluble pigment |
| Asparagin Agar medium | Middle | violetish white (13ba) | White (a) | None |
| Starch Inorganic salt Agar medium | Good | Slightly violetish white (13ba) | White (a) | None |
| Tyrosine Agar medium | Middle | Slightly violetish white (13ba) | Light orangish yellow (3ea) | None |
| Nutrient agar medium | Good | Slightly violetish white (13ba) | Light orangish yellow (3ea) | None |
| Yeast/malt Agar medium | Middle | Not formed | Light orangish yellow (3ea) | None |
| Oat meal Agar medium | Good | Not formed | Pale yellow (2db) | None |

(iii) Physiological property:

(1) Temperature range for growth (tested at each temperature of 20° C., 28° C., 33° C., 37° C., and 42° C. on yeast-maltose agar medium): grew at each temperature of 20° to 37° C., but not at 42° C.

(2) Liquefaction of gelatin (incubated at 20° C. using glucose-peptone-gelatin medium): positive (3) Hydrolysis of starch (starch-inorganic salt-agar medium): positive (4) Coagulation of skim milk and peptonization: slightly coagulated and peptonized (5) Formation of melanine-like pigment (on a tryptone-yeast extract-iron agar medium): slightly positive (iv) Utilization of various carbon sources (Pridham-Gottlieb agar medium):
  L-Arabinse: positive
  D-Xylose: positive
  D-Glucose: positive
  D-Fructose: positive
  Sucrose: positive
  Inositol: positive
  L-Rhamnose: positive
  Raffinose: slightly positive
  D-mannitol: positive Production of DCP-1 and DCP-2 of the present invention can be carried out by microbial conversion of the substrate aglycones with the aforesaid mutant strain culture grown in media which consist of a variety of nutrient sources to be generally utilized for actinomycetes. For example, as carbon sources, there can be used glucose, glycerin, sucrose, starch, maltose, animal and vegetable oils, etc., as nitrogen sources, there can be used, for example, organic nitrogens such as soy bean meal, meat extract, yeast extract, peptone, corn steep liquor, cotton seed meal, fish meal, etc. and inorganic nitrogens such as ammonium sulphate, ammonium chloride, sodium nitrate, ammonium phosphate, etc. If necessary and desired, sodium chloride, potassium chloride, potassium phosphates or bivalent metal salts such as $Mg^{++}$, $Ca^{++}$, $Zn^{++}$, $Fe^{++}$, $Cu^{++}$, $Mn^{++}$ or $Ni^{++}$, etc. and amino acids or vitamins can be added. In addition, for purpose of preventing foaming during fermentation, defoaming agents, for example, silicone (Shin-Etsu Kagaku, KK., KM 75, trademark), etc. can be appropriately added.

Aerobic fermentation in a liquid medium is preferred as in the case of the production of general other antibiotics and the cultivation can be carried out at temperatures from 25° to 32° C., preferably at 28° C. One embodiment of microbial conversion for production of the said compound is described hereinafter.

The strain of the present invention grown on a slant agar (yeast extract 0.3%, soluble starch 1.0% and agar 1.5%, pH 7.2) and then stocked at 5° to 7° C. is inoculated in a conventional liquid medium which consist of, for example, starch, glucose, organic nitrogen sources and inorganic salts and cultured therein at 25 to 32° C. for 24 to 72 hours under shaking or agitation condition in order to obtain a seed culture.

Then, the said seed culture is inoculated in a conventional fermentation medium, for example, comprising starch, maltose, dry yeast, soy bean meal and inorganic salts, in a concentration of 0.1 to 10% and cultivated at 25° to 32° C. for 48 to 96 hours under shaking or agitation condition, and then, α-citromycinone or β-isorhodomycinone is added thereto in a concentration of 10 to 300 μg/ml and cultivation is continued for further 48 to 96 hours to complete the microbial conversion.

The cultured broth thus obtained is separated into the mycelial cake and the filtrate, and the product is extracted from the cake and purified. For the extraction of the product from the mycelial cake, acetone, methanol, butanol or an acidic buffer (pH 2.0 to 4.0) is generally used, and the resulting extract is, after being concentrated, further extracted with a solvent such as chloroform, toluene, ethyl acetate, etc. The extract is thereafter concentrated to dryness to obtain a crude powder. For further purification, a gel-filtration, for example, with Sephadex LH-20 (crosslinked dextran gel, Pharmacia Fine Chemical AB, Co.) or column chromatography on CM-cellulose (carboxymethyl cellulose, Brown Co.) or an ion exchange resin, or a silica-gel thin-layer chromatography is advantageously utilized.

The pure compound thus obtained was identified to have the above-mentioned structure, as follows, by means of instrumental analyses including ultraviolet/visible ray absorption spectrum (hereinafter referred to as UV), infrared ray absorption spectrum (hereinafter referred to as IR), high resolving power $^1H$—NMR and $^{13}C$—NMR spectra, FD-mass spectrum, etc., and additionally by the instrumental analyses or silica-gel thin-layer chromatographic analysis of component sugar and aglycone which are obtained by mild acid hydrolysis.

Specifically, when α-citromycinone is used as the substrate for the microbial conversion, DCP-1 having the above-mentioned structural formula (I-a) where daunosamine is linked to the substrate added is obtained; and when β-isorhodomycinone is used as the substrate for the microbial conversion, DCP-2 having the above-mentioned structural formula (I-b) where daunosamine is linked to the substrate added is obtained.

Then, the preparation of the aglycone substrate for use in the examples to follow is set forth below, as a referential example.

REFERENTIAL EXAMPLE

Preparation of α-citromycinone:

A mutant SC-7 strain (deposited under FERM P-8720 on Mar. 31, 1986 at Fermentation Research Institute (Japan), Agency of Industrial Science and Technology, 1-3, Higashi, 1-chome, Yatabe-machi, Tsukuba-gun, Ibarakiken, Japan and transferred on Apr. 3, 1987 to international deposition FERM BP-1331 under the Treaty on the International Recognition of the Deposit of Microorganisms for the Purposes of Patent Procedure which was obtained by mutation of *Streptomyces violaceus* A262 strain, was cultured in a seed culture medium comprising 0.3% yeast extract and 1% soluble starch, pH 7.0 (100 ml/500 ml-Erlenmeyer flask) for 2 days by shaking culture, and this was inoculated into three jar fermentors (each having a capacity of 10 liters), to which five liters of a fermentation medium comprising 4% starch, 2.5% soy bean powder, 0.2% yeast extract, 0.25% salt, 0.32% $CaCO_3$, 0.001% $CuSO_4.5H_2O$, 0.00016% $FeSO_4.7H_2O$, 0.00032% $ZnSO_4.7H_2O$ and 0.00013% $MnCl_24.H_2O$, pH 7.0 had been put and sterilized, each in an amount of one rod (100 ml) and incubated for 5 days under the condition of an aeration of 5 liters/min., agitation of 350 rpm and a temperature of 28° C. The resulting broth (about 12 liters) was adjusted to pH 1.0 by addition of concentrated hydrochloric acid thereto and heated at 80° C. for 30 minutes. The mycelia was collected by centrifugation and extracted with 5 liters of acetone. The resulting acetone extract was evaporated to about 2 liters and extracted with 2 liters (total volume) of chloroform. The chloroform layer was evaporated to dryness to obtain 8.4 g of a crude powder containing α-citromycinone.

The total amount of the crude powder was put on a silica-gel column (diameter: 40 mm) packed with 200 g of silica-gel C-200 (manufactured by Wako Pure Chemical Industries, Ltd.) in chloroform, and eluted with 500 ml of chloroform, 1000 ml of a mixture solution of chloroform/menthol (500/1), 3000 ml of the mixture solution (400/1) and 2000 ml of the mixture solution (300/1). The fractions were cut in a volume of 10 ml and assayed for α-citromycinone by thin-layer chromatography. The α-citromycinone-containing fractions were pooled and evaporated to dryness to obtain 0.55 g of a pure yellow powder. The identification of the α-citromycinone was carried out by means of the UV and IR spectra, mass spectrum and $^1H$—NMR and $^{13}C$—NMR spectra thereof, referring to the standard value in the literature (Tetrahedron Letter, Vol. 8, page 28, 1968; and Chem. Ber., Vol. 10, page 1341, 1968).

On the other hand, for the preparation of β-isorhodomycinone, an obelmycin-producing strain SE2-2385 (FERM P-8165), as obtained by the mutation of the above-mentioned *Streptomyces violaceus* A262 strain, was fermented in the same scale and in the same manner as described above for the preparation of o-citromycinone by strain SC-7.

The resulting broth (about 12 liters) was similarly subjected to acid hydrolysis, acetone extraction from the mycelia and chloroform extraction, and finally 9.8 g of a crude powder containing β-isorhodomycinone. The whole amount of the crude powder was dissolved in 100 ml of methanol and the insoluble materials were centrifuged off. After concentration, the soluble fraction was applied on a silica-gel column (diameter: 78 mm) packed with 300 g of the above-mentioned silica-gel C-200 in chloroform, and eluted with 500 ml of chloroform, 100 ml of a mixture solution of chloroform/methanol (500/1), 3400 ml of the mixture solution (400/1) and 1000 ml of the mixture solution (300/1) in this order. β-isorhodomycinone was eluted with a mixture of chloroform/methanol (400/1). The β-isorhodomycinone-containing fractions were collected and evaporated to dryness followed by washing with ether The yield of β-isorhodomycinone was 0.62 g. The identification of this compound was carried out by means of $^1H$—M=NMR and $^{13}C$—NMR spectra and UV and FD mass spectra thereof, referring chemical data described in the literature (Chem. Ber., Vol. 98, page 3145, 1965).

Hereafter, the present invention will be described in more detail, referring to the examples below.

EXAMPLE 1

*Streptomyces* sp. D788, strain OXA-4 (FERM BP-8707) was grown on YS-slant agar (0.3% yeast extract, 1% soluble starch and 1.5% agar, pH 7.2) and inoculated into a 500 ml Erlenmeyer flasks containing each 100 ml of a seed medium as described below. Cultivation was carried out at 30° C. for 2 days on a rotary shaker (220 rpm).

| Seed Medium: | |
|---|---|
| Soluble starch | 0.5% |
| Glucose | 0.5% |
| Essan miit (soy bean meal, Ajinomoto Co.) | 1.0% |
| Yeast extract | 0.1% |
| NaCl | 0.1% |
| $K_2HPO_4$ | 0.1% |
| $MgSO_4.7H_2O$ | 0.1% |
| Tap water | pH 7.4 (before sterilization) |
| Sterilization: 120° C., 15 minutes | |

Then, the resulting seed culture was inoculated 2% in 800 Erlenmeyer flasks (capacity: 500 ml) each containing 50 ml of a fermentation medium having the composition to follow below and incubated at 28° C. for 96 hours on a rotary shaker (220 rpm).

| Fermentation Medium: | |
|---|---|
| Soluble starch | 5.0% |
| Maltose | 3.0% |
| Fish meal | 3.0% |
| Essan miit (aforesaid, soy bean meal) | 2.0% |
| Yeast extract | 0.2% |
| NaCl | 0.1% |
| $CaCO_3$ | 0.2% |
| $MgSO_4.7H_2O$ | 0.1% |
| $CuSO_4.5H_2O$ | 0.0007% |
| $FeSO_4.7H_2O$ | 0.001% |
| $MnCl_2.4H_2O$ | 0.0008% |
| $ZnSO_4.7H_2O$ | 0.0002% |
| | pH 7.5 (before sterilization) |
| Sterilization: 120° C., 15 minutes | |

These 800 fermentation flasks were divided into two parts, and a methanol solution of α-citromycinone (4 mg/ml) was added to one part (A group) comprising 400 flasks in an amount of 0.4 ml/flask, and these were continuously incubated for further 72 hours by shaking. On the other hand, a β-isorhodomycinone-methanol solution (4 mg/ml) was added to the other part (B group) comprising the remaining 400 flasks in an amount of 0.4 ml/flask, and these were similarly incubated for 72 hours by shaking.

EXAMPLE 2

The A group broth and the B group broth were collected, individually, and each of them was treated by the following process to obtain a crude powder containing DCP-1 or DCP-2 of the present invention, respectively.

Specifically, the mycelial cells were collected by centrifugation and were extracted with acetone (10 liters). After filtration, the resulting extract was concentrated under a reduced pressure to about 4 liters. The concentration was adjusted pH 3.5 with 6N-hydrochloric acid and washed twice with 700 ml of chloroform to remove the non-converted aglycone substrate. The aqueous layer was adjusted to pH 8.0 with 4N—NaOH and again extracted with chloroform (3 liters). After dehydrated with $Na_2SO_4$, the chloroform layer is concentrated to a small volume and an excess of ether was added thereto for precipitation, and the resulting precipitate was collected by centrifugation and dried in vacuum to obtain a crude powder. Yield: 300 mg from the A group broth and 250 mg from the B group broth.

EXAMPLE 3

The crude powder obtained from the A group in the Example 2 was dissolved in 10 ml of a mixture solution of methanol/chloroform (2/1) and subjected to gel-filtration on a Sephadex LH-20 column (diameter: 30×200 mm). The product DCP-1-containing fractions were pooled and concentrated to dryness and then chromatographed on a preparative silica-gel plates 60 $PF_{254}$ (Merck Co.) which were developed with a solvent system of chloroform/methanol/formic acid (40/10/1). DCP-1 band on the plates were scraped and extracted with a solvent mixture of chloroform/methanol (7/1), and the extract was concentrated and re-chromatographed on a preparative silica-gel thin-layer plates with a solvent mixture of chloroform/methanol/aqueous ammonia (50/10/1). The DCP-1 fractions were extracted from the silica-gel chromatogram with a solvent mixture of chloroform/methanol (7/1). The concentration to dryness gave 52 mg of yellow powder The purified yellow DCP-1 thus obtained was then dissolved in 10 ml of 1% acetic acid (pH 3.0) followed by washing with twice 4 ml of toluene. The aqueous layer was adjusted to pH 8.0 with saturated $NaHCO_3$ water and extracted with chloroform (50 ml). The chloroform layer was washed with saturated NaCl water, dehydrated over $Na_2SO_4$ and concentrated to a small volume. An excess of n-hexane was added to precipitate DCP-1, which was collected by centrifugation and dried in vacuum to obtain 42 mg of a pure DCP-1 powder.

| DCP-1: | | |
|---|---|---|
| (A) | Appearance: Yellow powder | |
| (B) | m.p.: 144 to 147° C. | |
| (C) | $[\alpha]_D^{25}$: +137° C. (c 0.02, in chloroform) | |
| (D) | Ultraviolet and visible ray absorption spectra: | |
| | $\lambda_{max}^{90\% \; methanol}$ nm($E_{1\;cm}^{1\%}$): | 204(429), 230(793), 257(530), 290sh(182), 435(246) |
| | $\lambda_{max}^{90\% \; methanol\text{-}0.01NHCl}$ nm($E_{1\;cm}^{1\%}$): | 204(435), 230(797), 257(532), 290sh(133), 435(247) |
| | $\lambda_{max}^{90\% \; methanol\text{-}0.01NNaOH}$ nm($E_{1\;cm}^{1\%}$): | 207(787), 240(753), 284(192), 498(189) |
| (E) | Infrared ray absorption spectrum (KBr)cm$^{-1}$: 3400, 2920, 1620, 1600, 1580, 1450, 1370, 1325, 1255, 1110, 1010, 980, 900 | |
| (F) | FD-MS spectrum: m/z 500 (M + H)$^+$ (Molecular weight 499.5 as $C_{26}H_{29}O_9N$) | |

| | -continued | |
|---|---|---|
| (G) | 400MHz $^1$H—NMR spectrum: | |
| | Proton | Chemical shift δ ppm |
| | 1-H | 7.82, d (J=8.0 Hz) |
| | 2-H | 7.69, t (J=8.0 Hz) |
| | 3-H | 7.32, d (J=8.0 Hz) |
| | 6-H | 7.78, s |
| | 7-H | 4.93, b |
| | 8-Ha | 2.29, dd (J=16.0 & 4.0 Hz) |
| | 8-Hb | 2.18, d (J=16.0 Hz) |
| | 10-H | 4.91, s |
| | 13-Ha | 1.85, q (J=8.0 Hz) |
| | 13-Hb | 1.72, q (J=8.0 Hz) |
| | 14-CH$_3$ | 1.11, t (J=8.0 Hz) |
| | 1'-H | 5.29, d (J=4.0 Hz) |
| | 2'-Ha | 1.85, t (J=12.0 Hz) |
| | 2'-Hb | 1.70, dd (J=12 & 4.0 Hz) |
| | 3'-H | 3.07, m |
| | 4'-H | 3.49, bs |
| | 5'-H | 4.08, q (J=7.0 Hz) |
| | 6'-CH$_3$ | 1.34, d (J=7.0 Hz) |

EXAMPLE 4

The crude powder obtained from the B group in the Example 2 was dissolved in 10 ml of a solvent mixture of methanol/chloroform (2/1) and subjected to gel filtration on a Sephadex LH-20 column (diameter: 30×200 mm). The product DCP-2 fraction was pooled, concentrated to dryness and then purified by a silica-gel C-200 column (diameter: 37 mm, 60 g) chromatography. The elution was carried out with 300 ml of a solvent mixture of chloroform/menthol (100/1), 250 ml of the same solvent mixture (50/1) and 500 ml of the solvent mixture (10/1) in this order. Fractionation wad done in a 10 ml volume. Fractions containing DCP-2 were pooled and evaporated to dryness. Further purification was carried out by preparative silica-gel thin-layer chromatography using silica-gel 60 $PF_{254}$ plates (Merck Co.) with a solvent system of chloroform/methanol/aqueous ammonia (50/10/1). The DCP-2 bands were scraped off and extracted with a solvent mixture of chloroform/methanol (7/1). The extract was evaporated to dryness and subjected to re-chromatography on preparative silica-gel 60 $PF_{254}$ plates using a solvent of chloroform/methanol/formic acid (40/10/1). The purified DCP-2 was recovered from the silica-gel plates by extracting with chloroform/methanol (7/1) and concentrated to dryness to give 38 mg of reddish powder.

The purified DCP-2 thus obtained was then dissolved in 10 ml of 1% acetic acid (pH 3.0) followed by washing with twice 4 ml of toluene. The aqueous layer was adjusted to pH 8.0 with saturated $NaHCO_3$ water and extracted with chloroform (30 ml). The chloroform layer was washed with saturated NaCl water, dehydrated over $Na_2SO_4$ and concentrated to a small volume. An excess of n-hexane was added to precipitate DCP-2, which was collected by centrifugation and dried in vacuum to obtain 29 mg of pure DCP-2 powder.

| DCP-2: | | |
|---|---|---|
| (A) | Appearance: Red-brown powder | |
| (B) | m.p.: 249 to 253° C. | |
| (C) | $[\alpha]_D^{25}$: +398° (c 0.004, in chloroform) | |
| (D) | Ultraviolet and visible ray absorption spectra: | |
| | $\lambda_{max}^{90\% \; methanol}$ nm($E_{1\;cm}^{1\%}$): | 203(345), 241(871), 297(134), |

| | | |
|---|---|---|
| | | 491sh(208), 523(340), 550(322), 562(342) |
| $\lambda_{max}^{90\% \text{ methanol-}0.01N HCl}$ | nm($E_1 \text{ cm}^{1\%}$): | 203(367), 241(878), 297(135), 491sh(215), 523(348), 550(325), 562(342) |
| $\lambda_{max}^{90\% \text{ methanol-}0.01N NaOH}$ | nm($E_1 \text{ cm}^{1\%}$): | 206(729), 244(858), 587(319), 627(322) |

(E) Infrared ray absorption spectrum (KBr) ν cm$^{-1}$
3400, 2920, 1590, 1460, 1405, 1305, 1260, 1190, 1015, 985, 800

(F) FD-MS spectrum: m/z 531 (M)$^+$
(Molecular weight 531.5 as $C_{26}H_{29}O_{11}N$)

(G) 400 MHz $^1$H—NMR spectrum:

| Proton | Chemical shift δ ppm |
|---|---|
| 2-H | 7.41, s |
| 3-H | 7.41, s |
| 7-H | 5.34, bs |
| 8-Ha | 2.23, d (J=16.0 Hz) |
| 8-Hb | 2.15, dd (J=16.0 & 4.0 Hz) |
| 10-H | 4.83, s |
| 13-Ha | 1.82, q (J=8.0 Hz) |
| 13-Hb | 1.74, q (J=8.0 Hz) |
| 14-CH$_3$ | 1.10, t (J=8.0 Hz) |
| 1'-H | 5.45, bs |
| 2'-CH$_2$ | 1.7, m |
| 3'-H | 2.93, bd |
| 4'-H | 3.46, s |
| 5'-H | 4.1 |
| 6'-CH$_3$ | 1.33, d |

What is claimed is:

1. An anthracycline antibiotic of the formula (I):

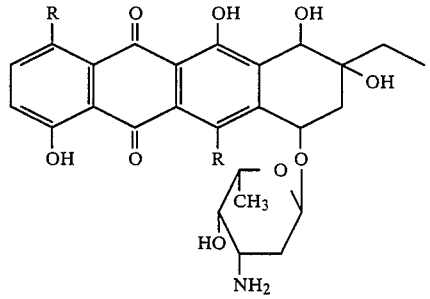

(where R represents a hydrogen atom or a hydroxyl group).

2. An anthracycline antibiotic as claimed in claim 1, which is represented by the formula (I-a):

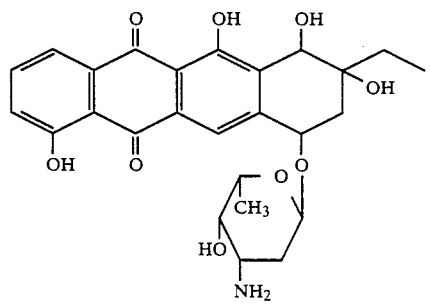

3. An anthracycline antibiotic as claimed in claim 1, which is represented by the formula (I-b):

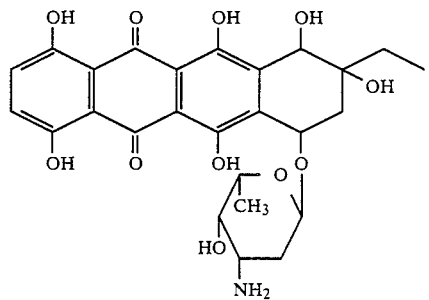

* * * * *